(12) United States Patent
Park et al.

(10) Patent No.: US 9,675,650 B2
(45) Date of Patent: Jun. 13, 2017

(54) **COMPOSITION FOR REMOVING KERATINOUS SKIN MATERIAL COMPRISING GREEN TEA *LACTOBACILLUS***

(71) Applicant: AMOREPACIFIC CORPORATION, Seoul (KR)

(72) Inventors: Joon Ho Park, Yongin-si (KR); Yeon Ju Hong, Yongin-si (KR); Il Young Kwack, Yongin-si (KR); Jong Won Shim, Yongin-si (KR); Jin Sup Shim, Yongin-si (KR); Kyeong Hwan Hwang, Yongin-si (KR); Young Gyu Kang, Yongin-si (KR); Myeong Hun Yeom, Yongin-si (KR); Jun Cheol Cho, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 81 days.

(21) Appl. No.: 14/430,316

(22) PCT Filed: Oct. 29, 2013

(86) PCT No.: PCT/KR2013/009679
§ 371 (c)(1),
(2) Date: Mar. 23, 2015

(87) PCT Pub. No.: WO2014/069874
PCT Pub. Date: May 8, 2014

(65) Prior Publication Data
US 2015/0246084 A1 Sep. 3, 2015

(30) Foreign Application Priority Data
Oct. 31, 2012 (KR) .................. 10-2012-0122143

(51) Int. Cl.
*A61K 36/82* (2006.01)
*A61K 35/747* (2015.01)
*C12R 1/25* (2006.01)
*A61Q 19/10* (2006.01)
*A61K 8/99* (2017.01)
*A61Q 19/00* (2006.01)
*A61K 8/02* (2006.01)

(52) U.S. Cl.
CPC .......... *A61K 35/747* (2013.01); *A61K 8/0212* (2013.01); *A61K 8/99* (2013.01); *A61K 36/82* (2013.01); *A61Q 19/00* (2013.01); *A61Q 19/10* (2013.01); *C12R 1/25* (2013.01); *A61K 2800/28* (2013.01)

(58) Field of Classification Search
None
See application file for complete search history.

(56) References Cited

U.S. PATENT DOCUMENTS

| 2005/0196480 | A1 | 9/2005 | Sullivan et al. |
| 2009/0022700 | A1 | 1/2009 | Cassin et al. |
| 2010/0166877 | A1* | 7/2010 | Baba ............... A23C 9/1234 424/535 |
| 2014/0106435 | A1* | 4/2014 | Kwack ................ C12R 1/25 435/252.9 |
| 2014/0301994 | A1* | 10/2014 | Klapper ............. A61Q 19/00 424/93.44 |

FOREIGN PATENT DOCUMENTS

| KR | 1020080026800 A | 3/2008 |
| KR | 1020090071998 A | 7/2009 |
| KR | 1020090104217 A | 10/2009 |
| KR | 1020100119692 A | 11/2010 |
| KR | 1020120019769 A | 3/2012 |
| KR | 1020120060296 A | 6/2012 |

OTHER PUBLICATIONS

Meyer et al., 2012 Poultry Science 91 :1506-1513.*
Di Cagno et al., Applied Microbiology and Biotechnology, Mar. 2010, vol. 86, Issue 2, pp. 731-741.*
International Search Report with English Translation for International Application No. PCT/KR2013/009679 dated Jan. 29, 2014.
Written Opinion for International Application No. PCT/KR2013/009679 dated Jan. 29, 2014.

* cited by examiner

*Primary Examiner* — Irene Marx
(74) *Attorney, Agent, or Firm* — Cantor Colburn LLP

(57) ABSTRACT

The present invention relates to a composition for removing keratinous skin material, the composition comprising a *Lactobacillus* strain or a culture thereof. Also, the present invention relates to a composition for removing keratinous skin material, the composition comprising green tea *Lactobacillus* as *Lactobacillus*. In contrast to when skin is improved through the supply of a moisture fraction by a commonly used skin-moisturizing component, the *Lactobacillus* according to the present invention removes keratinous skin material, thereby producing the advantageous effect that skin can be cared for and improved as the waste materials which accumulates on the skin is fundamentally removed. Therefore, the composition according to the present invention can effectively prevent or alleviate skin problems such as spots. Also, the invention regulates the skin and so improves skin tone by removing surplus keratinous material which is not needed by the skin.

6 Claims, 2 Drawing Sheets

COMPOSITION FOR REMOVING KERATINOUS SKIN MATERIAL COMPRISING GREEN TEA *LACTOBACILLUS*

TECHNICAL FIELD

The present disclosure relates to a novel use of *Lactobacillus* for skin.

BACKGROUND ART

*Lactobacillus* refers to the bacteria that produces lactic acid by degrading sugars such as glucose and is also called lactic acid bacteria. The lactic acid produced by *Lactobacillus* through lactic acid fermentation can inhibit the proliferation of pathogens and harmful bacteria and this property is utilized in foods such as dairy products, kimchi, brewed foods, etc. Also, since the *Lactobacillus* inhabits the gastrointestinal tracts of mammals and prevents undesired fermentation by harmful bacteria, they are importantly used in drugs for intestinal disorders.

Although *Lactobacillus* is widely used in foods including fermented foods, development in, for example, cosmetics or drugs is insufficient.

REFERENCES OF RELATED ART

Patent Document

Korean Patent Publication No. 10-2012-0019769 (Mar. 7, 2012).

DISCLOSURE

Technical Problem

The present invention is directed to providing a composition for removing keratinous skin material, which comprises *Lactobacillus* strain or a culture thereof, as a composition having a novel use for skin.

Technical Solution

In an aspect, the present invention provides a composition for removing keratinous skin material, which comprises *Lactobacillus* strain or a culture thereof.

In another aspect, the present invention provides a composition for removing keratinous skin material, which comprises green tea *Lactobacillus* strain or a culture thereof.

Advantageous Effects

The *Lactobacillus* according to the present invention has a very superior effect of removing keratinous skin material. Also, among the Lactobacilli according to the present invention, green tea *Lactobacillus* has excellent ability of degrading keratin which is the major component of the keratinous skin material and can effectively remove the keratinous skin material.

Accordingly, unlike the commonly used skin moisturizing agents which improve skin by supplying water, the *Lactobacillus* according to the present invention can manage and improve skin by removing keratinous skin material and thus fundamentally removing waste materials accumulated in the skin.

Therefore, the composition according to the present invention can effectively prevent or improve skin troubles such as acne. In addition, it can improve skin tone by removing the unnecessary keratinous skin material.

Accordingly, the composition according to the present invention can be widely utilized in the fields of cosmetics, cleansing and medicine.

BEST MODE

Figure 1:
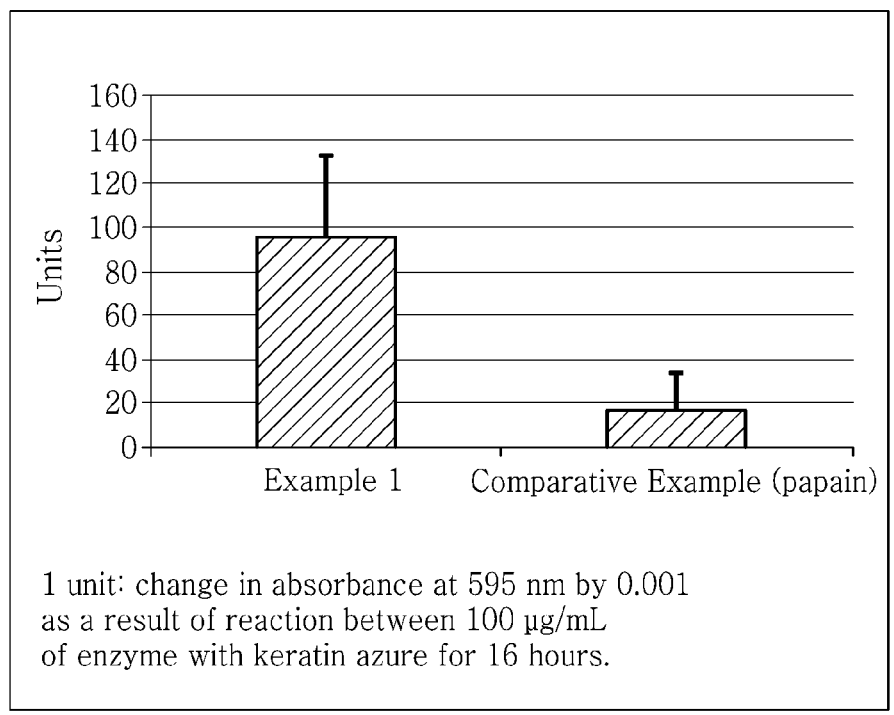
FIG. 1 shows a result of measuring the keratin degrading ability (absorbance at 595 nm) of *Lactobacillus* according to an exemplary embodiment of the present invention and a control substance.

In the present disclosure, "green tea *Lactobacillus*" refers to *Lactobacillus* isolated from *Camellia sinensis* (hereinafter, tea tree) in the family Theaceae and is used in the broadest sense, regardless of where it is derived, including leaves, buds, etc. of the tea tree, and regardless of how it is isolated.

Hereinafter, the present invention is described in detail.

An exemplary embodiment of the present invention provides a composition for removing keratinous skin material, which comprises *Lactobacillus* strain or a culture thereof.

Also, an exemplary embodiment of the present invention provides a composition for removing keratinous skin material, which comprises green tea *Lactobacillus* strain or a culture thereof.

Tea is commonly used as a beverage and is prepared by deactivating oxidases present in the bud or leaf of tea tree and removing water. Tea comprises vitamins, caffeine, tannins, flavonoids, essential oils, etc. and is used widely in foods and other applications.

The green tea *Lactobacillus* according to an exemplary embodiment of the present invention refers to *Lactobacillus* isolated from tea tree leaf and has very superior effect of degrading keratin, which is the major component of keratinous skin material, when applied to skin. Also, since it is a natural substance very slightly irritant to skin, it is suitable for removing the keratinous skin material.

The composition for removing keratinous skin material according to an exemplary embodiment of the present invention may comprise *Lactobacillus plantarum* as the *Lactobacillus* or the green tea *Lactobacillus*. Specifically, the *Lactobacillus plantarum* may be *Lactobacillus plantarum* APsulloc 331261 (Accession No.: KCCM11179P), *Lactobacillus plantarum* APsulloc 331263 (Accession No.: KCCM11180P), *Lactobacillus plantarum* APsulloc 331266 (Accession No.: KCCM11181P) or *Lactobacillus plantarum* APsulloc 331269 (Accession No.: KCCM11182P).

The APsulloc 331261, APsulloc 331263, APsulloc 331266 and APsulloc 331269 are the bacteria isolated from the leaf of tea tree (*Camellia sinensis*) and belong to

*Lactobacillus plantarum*. Specifically, each of the APsulloc 331261, APsulloc 331263, APsulloc 331266 and APsulloc 331269 may be isolated by: salting tea tree leaf with 5-15 wt % of salt based on the weight of the tea tree leaf; mixing the salted tea tree leaf with 0.1-3% of a sugar solution, e.g., fructo-oligosaccharide, and incubating at 25-35° C. for 1-5 days; and taking the culture at pH below 5 and incubating the same under an anaerobic condition at 25-35° C. for 1-5 days.

Also, the *Lactobacillus* comprised in the composition according to an exemplary embodiment of the present invention may be lyophilized *Lactobacillus* or a lyophilized lysate of *Lactobacillus* cells.

Specifically, the *Lactobacillus* comprised in the composition according to an exemplary embodiment of the present invention may be prepared by a method including the steps of: culturing *Lactobacillus* cells; removing insoluble material by centrifuging the cultured cells; and filtering and freeze-drying the resulting cell lysate.

The *Lactobacillus* strain or the culture thereof comprised in the composition according to an exemplary embodiment of the present invention has superior ability of degrading keratin, which is the major component of keratinous skin material, and thus can effectively remove the keratinous skin material. Accordingly, it is remarkably effective in removing wastes accumulated in skin. Also, the composition according to an exemplary embodiment of the present invention may prevent or improve skin troubles such as acne. In addition, the composition may improve skin tone by removing the unnecessary keratinous skin material.

In another exemplary embodiment of the present invention, the *Lactobacillus* strain or the culture thereof according to the present invention may be used to remove keratinous skin material. Also, in another exemplary embodiment of the present invention, the *Lactobacillus* strain or the culture thereof may be used to prevent or improve skin troubles and to improve skin tone.

Another exemplary embodiment of the present invention provides a method for removing keratinous skin material, which includes administering an effective amount of the *Lactobacillus* strain or the culture thereof according to the present invention as an active ingredient to a subject. Another exemplary embodiment of the present invention provides a method for preventing or improving skin troubles and to improve skin tone, which includes administering an effective amount of the *Lactobacillus* strain or the culture thereof as an active ingredient to a subject.

Another exemplary embodiment of the present invention provides the *Lactobacillus* strain or the culture thereof according to the present invention for use in the removal of keratinous skin material. Another exemplary embodiment of the present invention provides the *Lactobacillus* strain or the culture thereof according to the present invention for use in the prevention or improvement of skin troubles and improvement of skin tone.

Specifically, as an exemplary embodiment, the present invention provides a cosmetic composition for removing keratinous skin material, which comprises *Lactobacillus*, an extract thereof or a culture thereof.

The cosmetic composition may be provided in the form of any formulation suitable for topical application. Examples of the formulation may include solution, oil-in-water emulsion, water-in-oil emulsion, suspension, solid, gel, powder, paste, foam or aerosol. These formulations may be prepared according to methods commonly employed in the art.

The cosmetic composition may comprise, in addition to the active ingredient, other ingredients that may provide synergic effect to the desired main effect within a range not negatively affecting the main effect. The cosmetic composition according to the present invention may comprise substances selected from a group consisting of vitamins, polypeptides, polysaccharides and sphingolipids. Also, the cosmetic composition according to the present invention may comprise a humectant, an emollient, a surfactant, a UV absorbent, a preservative, a sterilizer, an antioxidant, a pH adjusting agent, an organic or inorganic pigment, a fragrance, a cooling agent or a deodorant. The amount of these ingredients may be determined easily by those skilled in the art within a range not negatively affecting the purpose and effect of the present invention. They may be added in an amount of 0.01-5 wt %, specifically 0.01-3 wt %, based on the total weight of the composition.

As another exemplary embodiment, the present invention provides a pharmaceutical composition for removing keratinous skin material, which comprises *Lactobacillus* strain, an extract thereof or a culture thereof.

The pharmaceutical composition may be provided in the form of any formulation suitable for topical application. Examples of the formulation may include solution for external application to skin, suspension, emulsion, gel, patch or spray, although not being limited thereto. These formulations may be prepared according to methods commonly employed in the art and may further comprise a surfactant, an excipient, a hydrant, an emulsification promoter, a suspending agent, a salt or buffer for osmotic pressure control, a colorant, a fragrance, a stabilizer, a preservative, an antiseptic or other commonly used adjuvants.

The administration dosage of the active ingredient in the pharmaceutical composition according to an exemplary embodiment of the present invention will vary depending on the age, sex and body weight of the subject, pathological condition and severity thereof, administration route or the discretion of a diagnoser. Determination of the dosage considering these factors is in the level of those skilled in the art. A daily dosage may be, for example, 0.1-5000 mg/kg/day, more specifically 50-500 mg/kg/day, although not being limited thereto.

The *Lactobacillus plantarum* APsulloc 331261, APsulloc 331263, APsulloc 331266 and APsulloc 331269 were accredited on Mar. 28, 2011 to the Korean Culture Center of Microorganisms under the Accession Nos. KCCM11179P, KCCM11180P, KCCM11181P and KCCM11182P.

Accredited agency: Korean Culture Center of Microorganisms (Korea).

Accession Nos.: KCCM11179P, KCCM11180P, KCCM11181P, KCCM11182P.

Accession date: Mar. 28, 2011.

[Mode for Invention]

Hereinafter, the present invention will be described in detail through examples. However, the following examples are for illustrative purposes only and it will be apparent to those of ordinary skill in the art that the scope of the present invention is not limited by the examples.

Also, it will be apparent that various changes and modifications can be made to the appended claims without departing from the scope of the present invention.

[Example 1] Preparation of *Lactobacillus* Isolated from Tea Tree Leaf (*Lactobacillus plantarum* APsulloc 331261)

Isolation of *Lactobacillus plantarum* APsulloc 331261

Among the Lactobacilli according to an exemplary embodiment of the present invention, *Lactobacillus plantarum* APsulloc 331261 was isolated as follows.

200 g of tea tree leaf was washed 2 times with primarily distilled water to remove impurities. After removing water from the washed tea tree leaf, it was mixed with 8 wt % of salt based on the weight of the tea tree leaf and kept at room temperature for 3 hours. The salted tea tree leaf was mixed with 1000 mL of a 1% fructo-oligosaccharide solution and incubated for 3 days in an incubator at 32° C. 3 days later, it was checked whether the pH of the culture decreased below 5. The culture at pH below 5 was taken and incubated in a Difco Lactobacilli MRS Agar® medium. The incubation was performed for 2 days in a chamber at 32° C. under anaerobic condition and the white colony was taken.

As a result, *Lactobacillus plantarum* APsulloc 331261 was isolated from the tea tree leaf.

Preparation of *Lactobacillus plantarum* APsulloc 331261 Powder

The *Lactobacillus plantarum* APsulloc 331261 was prepared into powder as follows.

The *Lactobacillus plantarum* APsulloc 331261 isolated from the tea tree leaf was cultured at pH 6.2 for two days and the cells were collected after centrifugation. The cells were washed to remove the medium components and impurities treated with a lytic enzyme and then incubated at 40° C. for a day. After removing insoluble material from the cell lysate through centrifugation, followed by filtration through a membrane and lyophilization, the *Lactobacillus plantarum* APsulloc 331261 was obtained in the form of powder.

[Example 2] Preparation of *Lactobacillus* Isolated from Tea Tree Leaf (*Lactobacillus plantarum* APsulloc 331263)

Isolation of *Lactobacillus plantarum* APsulloc 331263

As another exemplary embodiment of the present invention, *Lactobacillus plantarum* APsulloc 331263 was isolated as follows.

200 g of tea tree leaf was washed 2 times with primarily distilled water to remove impurities. After removing water from the washed tea tree leaf, it was mixed with 8 wt % of salt based on the weight of the tea tree leaf and kept at room temperature for 3 hours. The salted tea tree leaf was mixed with 1000 mL of a 1% fructo-oligosaccharide solution and incubated for 3 days in an incubator at 32° C. 3 days later, it was checked whether the pH of the culture decreased below 5. The culture at pH below 5 was taken and incubated in a Difco Lactobacilli MRS Agar® medium. The incubation was performed for 2 days in a chamber at 32° C. under anaerobic condition and the white colony was taken.

As a result, *Lactobacillus plantarum* APsulloc 331263 was isolated from the tea tree leaf.

Preparation of *Lactobacillus plantarum* APsulloc 331263 Powder

The *Lactobacillus plantarum* APsulloc 331263 was prepared into powder as follows.

The *Lactobacillus plantarum* APsulloc 331263 isolated from the tea tree leaf was cultured at pH 6.2 for two days and the cells were collected after centrifugation. The cells were washed to remove the medium components and impurities treated with a lytic enzyme and then incubated at 40° C. for a day. After removing insoluble material from the cell lysate through centrifugation, followed by filtration through a membrane and lyophilization, the *Lactobacillus plantarum* APsulloc 331263 was obtained in the form of powder.

[Example 3] Preparation of *Lactobacillus* Isolated from Tea Tree Leaf (*Lactobacillus plantarum* APsulloc 331266)

Isolation of *Lactobacillus plantarum* APsulloc 331266

As another exemplary embodiment of the present invention, *Lactobacillus plantarum* APsulloc 331266 was isolated as follows.

200 g of tea tree leaf was washed 2 times with primarily distilled water to remove impurities. After removing water from the washed tea tree leaf, it was mixed with 8 wt % of salt based on the weight of the tea tree leaf and kept at room temperature for 3 hours. The salted tea tree leaf was mixed with 1000 mL of a 1% fructo-oligosaccharide solution and incubated for 3 days in an incubator at 32° C. 3 days later, it was checked whether the pH of the culture decreased below 5. The culture at pH below 5 was taken and incubated in a Difco Lactobacilli MRS Agar® medium. The incubation was performed for 2 days in a chamber at 32° C. under anaerobic condition and the white colony was taken.

As a result, *Lactobacillus plantarum* APsulloc 331266 was isolated from the tea tree leaf.

Preparation of *Lactobacillus plantarum* APsulloc 331266 Powder

The *Lactobacillus plantarum* APsulloc 331266 was prepared into powder as follows.

The *Lactobacillus plantarum* APsulloc 331266 isolated from the tea tree leaf was cultured at pH 6.2 for two days and the cells were collected after centrifugation. The cells were washed to remove the medium components and impurities treated with a lytic enzyme and then incubated at 40° C. for a day. After removing insoluble material from the cell lysate through centrifugation, followed by filtration through a membrane and lyophilization, the *Lactobacillus plantarum* APsulloc 331266 was obtained in the form of powder.

[Example 4] Preparation of *Lactobacillus* Isolated from Tea Tree Leaf (*Lactobacillus plantarum* APsulloc 331269)

Isolation of *Lactobacillus plantarum* APsulloc 331269

As another exemplary embodiment of the present invention, *Lactobacillus plantarum* APsulloc 331269 was isolated as follows.

200 g of tea tree leaf was washed 2 times with primarily distilled water to remove impurities. After removing water from the washed tea tree leaf, it was mixed with 8 wt % of salt based on the weight of the tea tree leaf and kept at room temperature for 3 hours. The salted tea tree leaf was mixed with 1000 mL of a 1% fructo-oligosaccharide solution and incubated for 3 days in an incubator at 32° C. 3 days later, it was checked whether the pH of the culture decreased below 5. The culture at pH below 5 was taken and incubated in a Difco Lactobacilli MRS Agar® medium. The incubation was performed for 2 days in a chamber at 32° C. under anaerobic condition and the white colony was taken.

As a result, *Lactobacillus plantarum* APsulloc 331269 was isolated from the tea tree leaf.

Preparation of *Lactobacillus plantarum* APsulloc 331269 Powder

The *Lactobacillus plantarum* APsulloc 331269 was prepared into powder as follows.

The *Lactobacillus plantarum* APsulloc 331269 isolated from the tea tree leaf was cultured at pH 6.2 for two days and the cells were collected after centrifugation. The cells were washed to remove the medium components and impurities treated with a lytic enzyme and then incubated at 40° C. for a day. After removing insoluble material from the cell lysate through centrifugation, followed by filtration through a membrane and lyophilization, the *Lactobacillus plantarum* APsulloc 331269 was obtained in the form of powder.

[Test Example 1] Evaluation of Ability of Removing Keratinous Skin Material

In order to evaluate the ability of removing keratinous skin material of the *Lactobacillus* according to an exemplary embodiment of the present invention, the ability of degrading keratin, which is the major component of the keratinous skin material, was measured.

To measure the keratin degrading ability, keratin azure was used as a substrate and color change caused by the azo dye produced as the substrate is enzymatically degraded was measured. The powder of Example 1 was used as an exemplary embodiment of the present invention and papain powder, which is widely used in care products for keratinous skin material, was used as a control substance.

First, 100 µg/mL of Example 1 or the control substance was dissolved in pH 5.0 acetate buffer and, after adding 0.5% of keratin azure, the mixture was incubated in a shaking incubator at 37° C. for 3 hours. Then, after stopping the reaction by heating in a boiling water bath, followed by filtering through a 0.45 µm filter, absorbance was measured at 595 nm. For comparison, the amount of proteins in the reaction sample was measured by Bradford assay. The result is shown in FIG. 1.

As seen from FIG. 1, Example 1 according to the present invention showed the change in absorbance at 595 nm corresponding to 95 units, whereas the papain showed change corresponding to about 16 units, indicating that keratin was degraded about 5 times or more for Example 1 than for the papain as the control substance.

Accordingly, it was confirmed that the *Lactobacillus* of the present invention exhibits remarkably superior ability of removing keratinous skin material than papain which is widely used in care products for keratinous skin material.

[Test Example 2] Comparison of Keratin Degrading Ability of Lactobacilli

In order to evaluate the ability of removing keratinous skin material of Lactobacilli, the ability of degrading keratin, which is the major component of the keratinous skin material, was measured and compared.

For the Lactobacilli, *Lactobacillus plantarum* APsulloc 331261 (Accession No. KCCM11179P; hereinafter, green tea *Lactobacillus*), *Lactobacillus acidophilus* (Accession No. KCCM41619; hereinafter, kimchi *Lactobacillus*) and *Lactobacillus bulgaricus* (Accession No. KCCM40266; hereinafter, milk *Lactobacillus*) were used.

Figure 2:
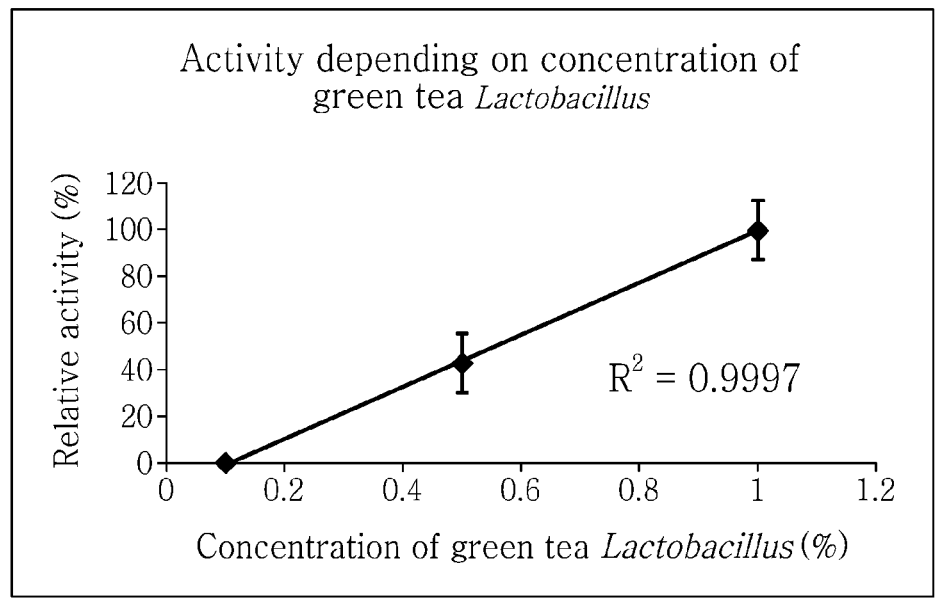
FIG. 2 shows a result of measuring the relative keratin degrading activity for different concentration of *Lactobacillus* isolated from tea tree leaf according to an exemplary embodiment of the present invention.

First, the keratin degrading ability depending on the concentration of the green tea *Lactobacillus* was measured in the same manner as in Test Example 1. The activity of keratin degrading ability measured when 10 mg of the green tea *Lactobacillus* powder was dissolved in 1 mL of pH 5.0 acetate buffer (1 w/v %) was set to be 100. Then, the relative activity for different concentrations of the green tea *Lactobacillus* powder was measured (FIG. 2).

Subsequently, the keratin degrading ability of kimchi *Lactobacillus* powder and milk *Lactobacillus* powder was measured in the same manner as in Test Example 1 by dissolving 10 mg of each of the *Lactobacillus* powder in 1 mL of pH 5.0 acetate buffer (1 w/v %). The relative activity with respect to the keratin degrading ability of 1 w/v % green tea *Lactobacillus* powder as 100 is shown in FIG. 3.

Figure 3:
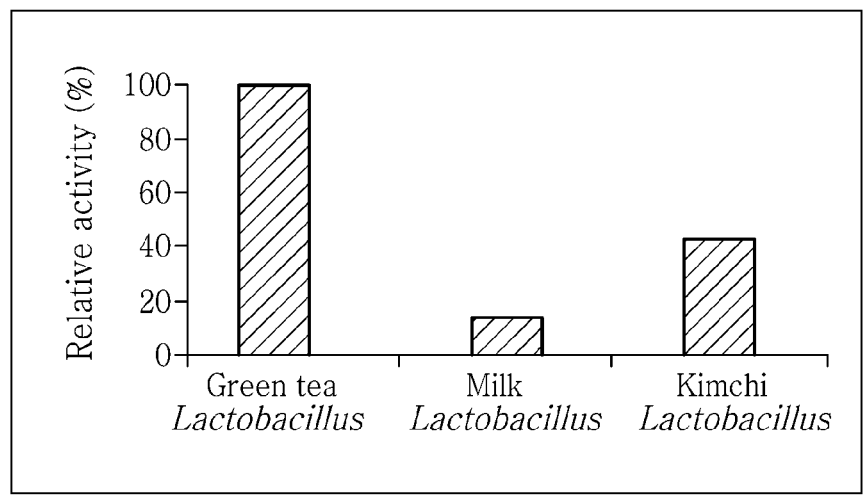
FIG. 3 shows a result of comparing the relative keratin degrading activity of *Lactobacillus* isolated from tea tree leaf according to an exemplary embodiment of the present invention, *Lactobacillus* isolated from milk and *Lactobacillus* isolated from kimchi.

As seen from FIG. 3, the keratin degrading ability of milk *Lactobacillus* was only about 15% and that of kimchi *Lactobacillus* was only about 40%, with respect to that of green tea *Lactobacillus* as 100% at the same concentration. Accordingly, it was confirmed that, among the *Lactobacillus*, the *Lactobacillus* isolated from tea tree leaf exhibits very superior ability of degrading keratinous skin material as compared to the *Lactobacillus* isolated from kimchi or milk.

[Test Example 3] Ability of Removing Keratinous Skin Material of Green Tea Lactobacilli In order to compare the ability of removing keratinous skin material of the green tea Lactobacilli according to an exemplary embodiment of the present invention, the ability of degrading keratin, which is the major component of the keratinous skin material, was measured.

For the Lactobacilli, *Lactobacillus plantarum* APsulloc 331261 (Accession No. KCCM11179P, Example 1), *Lactobacillus plantarum* APsulloc 331263 (Accession No. KCCM11180P, Example 2), *Lactobacillus plantarum* APsulloc 331266 (Accession No. KCCM11181P, Example 3) and *Lactobacillus plantarum* APsulloc 331269 (Accession No. KCCM11182P, Example 4) were used.

First, as described in Test Example 1, 100 µg/mL of each of Examples 1-4 was dissolved in pH 5.0 acetate buffer and, after adding 0.5% of keratin azure, the mixture was incubated in a shaking incubator at 37° C. for 3 hours. Then, after stopping the reaction by heating in a boiling water bath, followed by filtering through a 0.45 µm filter, absorbance was measured at 595 nm. For comparison, the absorbance was measured in the absence of *Lactobacillus* (control) in the same manner.

The absorbance measured for Example 1 subtracted by the absorbance of the control group was set to be 100 as relative activity. The absorbance measured for Examples 2-4 was also subtracted by the absorbance of the control group and their relative activity was calculated with respect to that of Example 1 as 100. The result is shown in FIG. 4.

Figure 4:
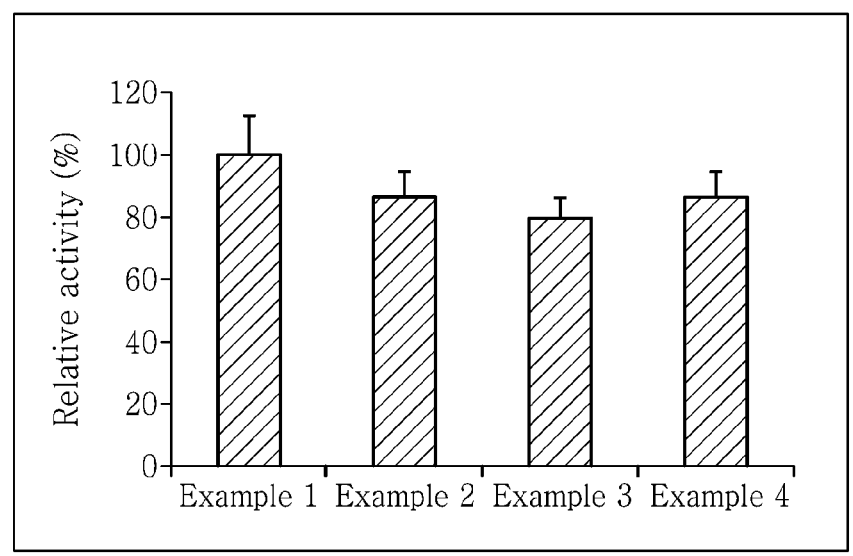
FIG. 4 shows a result of comparing the relative keratin degrading activity of Lactobacilli isolated from tea tree leaf according to an exemplary embodiment of the present invention.

As seen from FIG. 4, among Examples 1-4 according to the present invention, Example 1 (*Lactobacillus plantarum* APsulloc 331261) showed the highest relative activity. However, all the green tea Lactobacilli of Examples 1-4 according to the present invention showed similar relative activity in the range between 0.005 and 0.007. Considering that Example 1 showed superior ability of removing keratinous skin material as compared to papain, kimchi *Lactobacillus* or milk *Lactobacillus* in Test Examples 1-2, it is expected the other Lactobacilli according to the present invention will also exhibit superior ability of removing keratinous skin material.

Hereinafter, the present invention will be described in detail through formulation examples. However, the following formulation examples are for illustrative purposes only and it will be apparent to those of ordinary skill in the art that the scope of the present invention is not limited by the formulation examples.

[Formulation Example 1] Nourishing Lotion

A nourishing lotion was prepared with the composition described in Table 1 according to a commonly employed method.

TABLE 1

| Ingredients | Contents (wt %) |
|---|---|
| Purified water | Balance |
| Glycerin | 8.0 |
| Butylene glycol | 4.0 |
| Hyaluronic acid extract | 5.0 |
| β-Glucan | 7.0 |
| Carbomer | 0.1 |
| Green tea *Lactobacillus* powder of Example 1 | 0.05 |
| Caprylic/capric triglyceride | 8.0 |
| Squalane | 5.0 |
| Cetearyl glucoside | 1.5 |
| Sorbitan stearate | 0.4 |
| Cetearyl alcohol | 1.0 |
| Preservative | Adequate |
| Fragrance | Adequate |
| Pigment | Adequate |
| Triethanolamine | 0.1 |
| Total | 100 |

[Formulation Example 2] Nourishing Cream

A nourishing cream was prepared with the composition described in Table 2 according to a commonly employed method.

TABLE 2

| Ingredients | Contents (wt %) |
|---|---|
| Purified water | Balance |
| Glycerin | 3.0 |
| Butylene glycol | 3.0 |
| Liquid paraffin | 7.0 |
| β-Glucan | 7.0 |
| Carbomer | 0.1 |
| Green tea *Lactobacillus* powder of Example 2 | 3.0 |
| Caprylic/capric triglyceride | 3.0 |
| Squalane | 5.0 |
| Cetearyl glucoside | 1.5 |
| Sorbitan stearate | 0.4 |
| Polysorbate 60 | 1.2 |
| Preservative | Adequate |
| Fragrance | Adequate |
| Pigment | Adequate |
| Triethanolamine | 0.1 |
| Total | 100 |

[Formulation Example 3] Massage Cream

A massage cream was prepared with the composition described in Table 3 according to a commonly employed method.

TABLE 3

| Ingredients | Contents (wt %) |
|---|---|
| Purified water | Balance |
| Glycerin | 8.0 |
| Butylene glycol | 4.0 |
| Liquid paraffin | 45.0 |
| β-Glucan | 7.0 |
| Carbomer | 0.1 |
| Green tea *Lactobacillus* powder of Example 3 | 1.0 |
| Caprylic/capric triglyceride | 3.0 |
| Beeswax | 4.0 |
| Cetearyl glucoside | 1.5 |
| Sorbitan sesquioleate | 0.9 |
| Vaseline | 3.0 |
| Preservative | Adequate |

TABLE 3-continued

| Ingredients | Contents (wt %) |
|---|---|
| Fragrance | Adequate |
| Pigment | Adequate |
| Paraffin | 1.5 |
| Total | 100 |

[Formulation Example 4] Pack

A pack was prepared with the composition described in Table 4 according to a commonly employed method.

TABLE 4

| Ingredients | Contents (wt %) |
|---|---|
| Purified water | Balance |
| Glycerin | 4.0 |
| Polyvinyl alcohol | 15.0 |
| Hyaluronic acid extract | 5.0 |
| β-Glucan | 7.0 |
| Allantoin | 0.1 |
| Green tea *Lactobacillus* powder of Example 4 | 0.5 |
| Nonyl phenyl ether | 0.4 |
| Polysorbate 60 | 1.2 |
| Preservative | Adequate |
| Fragrance | Adequate |
| Pigment | Adequate |
| Ethanol | 6.0 |
| Total | 100 |

[Formulation Example 5] Ointment

An ointment was prepared with the composition described in Table 5 according to a commonly employed method.

TABLE 5

| Ingredients | Contents (wt %) |
|---|---|
| Purified water | Balance |
| Glycerin | 8.0 |
| Butylene glycol | 4.0 |
| Liquid paraffin | 15.0 |
| β-Glucan | 7.0 |
| Carbomer | 0.1 |
| Green tea *Lactobacillus* powder of Example 1 | 1.0 |
| Caprylic/capric triglyceride | 3.0 |
| Squalane | 1.0 |
| Cetearyl glucoside | 1.5 |
| Sorbitan stearate | 0.4 |
| Cetearyl alcohol | 1.0 |
| Preservative | Adequate |
| Fragrance | Adequate |
| Pigment | Adequate |
| Beeswax | 4.0 |
| Total | 100 |

[Accession Number]

Accredited agency: Korean Culture Center of Microorganisms (Korea).

Accession Nos.: KCCM11179P, KCCM11180P, KCCM11181P, KCCM11182P.

Accession date: Mar. 28, 2011.

The invention claimed is:

1. A method for removing keratinous skin material comprising administering an effective amount of one or more *Lactobacillus plantarum* strains or a culture thereof as the active ingredient to a subject, wherein the method removes keratinous skin material, comprising administering an effective amount of *Lactobacillus* strain or a culture thereof as an active ingredient to a subject, wherein the method is for removing keratinous skin material, wherein the *Lactobacillus plantarum* is selected from a group consisting of *Lactobacillus plantarum* APsulloc 331261 (Accession No.: KCCM11179P), *Lactobacillus plantarum* APsulloc 331263 (Accession No.: KCCM11180P), *Lactobacillus plantarum* APsulloc 331266 (Accession No.: KCCM11181P), and *Lactobacillus plantarum* APsulloc 331269 (Accession No.: KCCM11182P).

2. The method according to claim 1, wherein the active ingredient is lyophilized.

3. The method according to claim 1, wherein the active ingredient is a lyophilized lysate of cells.

4. The method according to claim 1, wherein the active ingredient is prepared by a method comprising:
 (a) culturing cells;
 (b) removing insoluble material by centrifuging the cultured cells; and
 (c) filtering and freeze-drying the cell lysate obtained in (b).

5. The method according to claim 1, wherein the active ingredient removes keratinous skin material by degrading keratin.

6. The method according to claim 1, wherein the method improves skin tone.

\* \* \* \* \*